United States Patent [19]
Robertson

[11] Patent Number: 5,426,790
[45] Date of Patent: Jun. 27, 1995

[54] SUN SHIELD FOR HEAD WEAR

[76] Inventor: Stanley Robertson, P.O. Box 2273, Key Largo, Fla. 33037

[21] Appl. No.: 201,562

[22] Filed: Feb. 25, 1994

[51] Int. Cl.⁶ .............................................. A42B 1/24
[52] U.S. Cl. ...................................... 2/209.13; 2/209
[58] Field of Search ............... 2/2, 195.1, 172, 175.1, 2/209, 209.11, 209.12, 209.13, 423; 181/129, 133

[56] References Cited
U.S. PATENT DOCUMENTS

| | | | |
|---|---|---|---|
| 280,005 | 6/1883 | Beard et al. | 2/209.13 |
| 379,965 | 3/1888 | Lippincott | 2/172 |
| 869,401 | 10/1907 | Wells | 2/209.13 |
| 2,447,078 | 8/1948 | Maxant | 2/209 |

Primary Examiner—Clifford D. Crowder
Assistant Examiner—Diana L. Biefeld

[57] ABSTRACT

Apparatus for protecting a person's ears from the damaging ultra-violet rays of the sun is presented. The ear protector apparatus conveniently clips to the outside of a cap, typically, a baseball cap. The protective ear apparatus is positionable along the headband of the cap in accordance with the anatomical configuration of a person's head. Furthermore, the protective ear apparatus is removable and may be applied from one cap to another. Ornamental designs may be applied to the outside surface of the ear protector to display the logo of a sports team or even to advertise an organization or business entity.

9 Claims, 3 Drawing Sheets

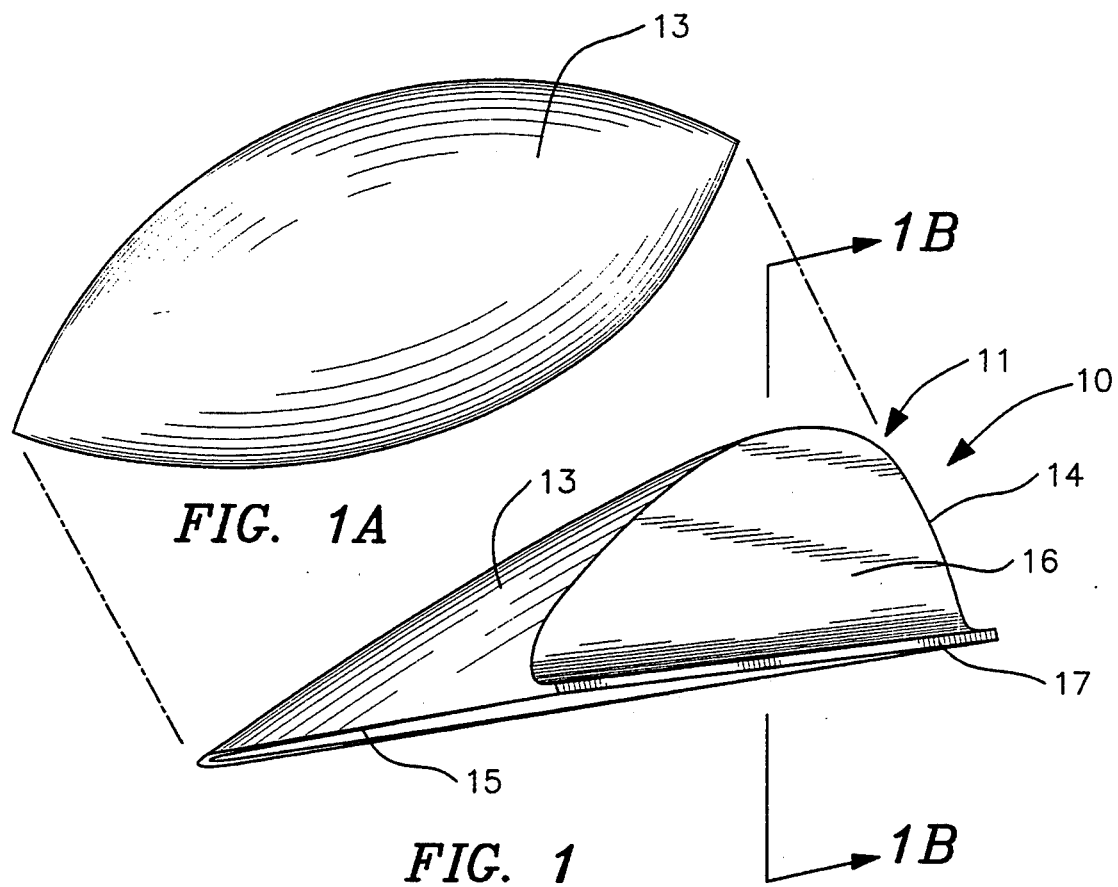
FIG. 1A
FIG. 1
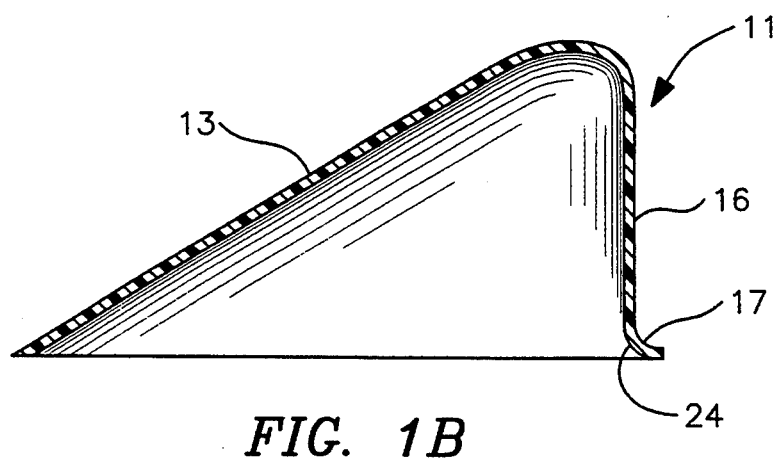
FIG. 1B

SUN SHIELD FOR HEAD WEAR

BACKGROUND OF THE INVENTION

1. Field of the Invention

This invention relates in general to headwear and in particular to removable apparatus adapted to be affixed to headwear which primarily serves to protect a person's ears from harmful ultra-violet rays emitted by the sun.

2. Description of the Prior Art

The devastating effect of the sun's rays has been known for many years. The initial observable effect was of course, burning of the skin due to mere exposure to the sun. The so called suntan which is often advertised as being a healthy look is in fact actual burning of the skin by the sun's rays. In tropical or desert environments, because the sun's rays are more intense, the burning effect of the sun is also more intense. Articles of clothing such as hats, shirts and pants or trousers serve well to protect a person from sunburns. Unprotected portions of a person's body, however, were not adequately protected by such articles of clothing and hence, out of necessity the hat neck flap was invented and is exemplified by the highly known cap of the french foreign legion. While not necessarily the first headwear to use such a flap, the French foreign legion cap is extremely well known and quite adequately serves its intended purpose. The headgear being referred to comprises a cap having a peak or bill in the front thereof with an extra piece of material or flap sewn into the headband extending around primarily the back thereof to cover both the neck and the ears of the person wearing the hat.

The French foreign legion protective headgear and its variations such as simple handkerchief held in place by a bill cap and extending over a person's neck, while quite effective, are not in wide spread use today. While one can only speculate as to just why such protective headgear is not in general use today, one reason might be, that unless it is being worn in the sun, people do not want to wear a hat with a flap in the back. To counter this, it might be said that all that is required is to simply pull the flap up into the hat during periods of no sun. Such solutions obviously not satisfactory or else people would be wearing the same. Accordingly, there exists a need to provide protective headgear for persons to prevent being sunburned in exposed areas.

More recently, the harmful effect of the sun's ultraviolet rays has come into focus. Skin cancer due to the ultraviolet rays has become a prime concern for people in recent years. That this is so, because people have become more health conscious is of no avail, because the fact is that the ultraviolet rays of the sun does cause skin cancer. Again, it is the exposed portions of a person'body that is subject to skin cancer by the sun's rays. This again includes the ears and neck of a person's body. The prior art known to the inventor herein serving to protect a person's skin from sunburn as well as possible cancer, generally involves the use of flaps either flexible or non-flexible, removably attached to a hat headband or a headband which may be worn in conjunction with a cap which flaps cover a person's neck and ears.

The obvious prior art attempt to utilize a removable flap attached to a headgear or cap involves the use of a hook and loop attachment method so that the flap may be attached and removed from the cap. Such removable flaps give one the appearance of being dressed in a french foreign legion hat which apparently does not appeal to people because the same is not in very much use today. Other prior art attempts include flaps in addition to being removable are hinged so that they may be rotated upwardly and out of position when there are no sun's rays or the rays are not particularly intense. Again, such protective headgear is not in widespread use.

Accordingly, notwithstanding the prior art, there exists a definite need for apparatus to be adapted to be attached to a billed cap which shields a person from the harmful effects of the sun's rays. Preferably, such protective apparatus should be removable so that the cap may be worn without the protective apparatus.

Accordingly, a primary object of the present invention is to provide apparatus which may be removably attached to a billed cap and serve to protect a person's ears and neck from the harmful effect of the sun's rays.

Another object of the present invention is to provide protective ear and neck apparatus which is small and unobtrusive so as to be aesthetically pleasing, yet functional.

Another object of the present invention is to provide ear and neck protectors adapted to be fitted to a billed cap which when removed leaves the cap in an original or unaltered state.

Another object of the present invention is to provide ear and neck protective apparatus which may be adjustable positioned around the headband of a billed cap so as to adapt the same to be fitted to a particular person's head anatomy.

Another object of the present invention is to provide ear and neck protective apparatus which is readily adaptable to be fitted with ornamental decorations and/or to convey various visual statements.

Yet another object of the present invention is to provide ear and neck protective apparatus which may be transferred to one cap to another and yet be effective for the function intended.

The above state objects as well as others, which, although not specifically stated, but are intended to be included within the present invention, are accomplished by the present invention and will become apparent from the hereinafter set forth detailed description of the invention, drawings, and the claims appended herewith.

SUMMARY OF THE INVENTION

The present invention accomplishes the above stated objectives as well as others in accordance with a fair reading of the entire specification including the claims and drawings appended hereto.

Apparatus for protecting a person's ears from the damaging ultra-violet rays of the sun is presented. The ear protector apparatus conveniently clips to the outside of a cap, typically, a baseball cap, and is held in place thereon by a clip. The protective ear apparatus is positionable along the headband of the cap in accordance with the anatomical configuration of a person's head. Furthermore, the protective ear apparatus is removable and may be applied to the outside surface of the ear protector to display the logo of a sports team or even to advertise an organization or business entity.

The inventive ear protector apparatus comprises an ear protector member having a convexly curved outer portion having a football-like shape and an inner portion which is fixedly attached to the interior rim of the outer portion and extends along the length thereof, and a clip member. The bottom end of the inner portion of the ear protector member includes a small flange-like member. The flange member being adapted to fit under the bottom rim or edge of the headband of the cap to which the protective ear apparatus is to be applied. The clip member has a cross-section which somewhat resembles the letter "J" and which is configured to hook over the bottom flange of the ear protector member and extend upwardly against the inner portion of the cap. Serrated edges may be applied to a portion of the clip member which is contact with the inside of the headband. Spring characteristics of the clip provide the securing force to keep the ear protector apparatus in place on the cap. In adapting the apparatus to a cap, the ear protector member is first positioned, then the spring clip member is snapped in place thereby securing the ear protector to the cap.

BRIEF DESCRIPTION OF THE DRAWINGS

Various other objects, advantages and features of the invention will become apparent to those skilled in the art from the following discussion taken in conjunction with the following drawings, in which:

FIG. 1 is an isometric view of the ear protector apparatus in accordance with present invention;

FIG. 1A is a plan view of the outside shape of the ear protector apparatus.

FIG. 1B is a cross-sectional view taken along the line 1B—1B of FIG. 1;

DESCRIPTION OF THE PREFERRED EMBEDMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 2:
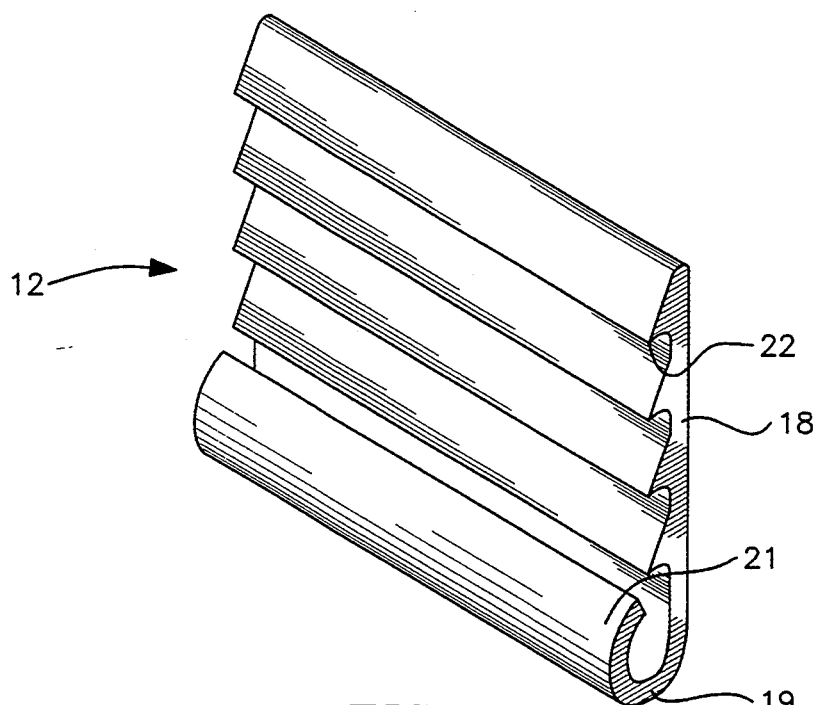
FIG. 2 is an isometric view of the clip portion of the ear protector apparatus in accordance with the present invention.

Referring now to FIGS. 1 and 2 of the drawings, the inventive ear protector apparatus is designated in general by the numeral 10. The ear protector apparatus 10 includes an outer ear protecting member 11 and a clip member 12. Outer member 11 comprises a first portion 13 having a convexly curved shape which in plan view resembles the shape of the football having two curved edges intersecting with each other at opposite ends thereof. (See FIG. 1A). The cross-sectional shape of ear protector 11 is shown in FIG. 1B. For purposes of this description, the edge of outer member 11 which is to be positioned against the side of the cap will be designated as the vertical edge 14, while the other edge will be designated as the horizontal edge 15. Fixedly attached to the vertical edge 14 is a plate member 16 having a concave shape which is configured to be placed against the convex shape of a cap to which the inventive apparatus is to be applied. The concave plate 16 includes a flange member 17 extending along the bottom unattached end 24 thereof. Flange member 17 extends substantially horizontally inward toward the cap to which the device is to be applied having an inner radius of a small dimension so as to fit therein the lower edge of a headband of a cap. Outer member 11 may be made from a suitable material such as plastic or metal which may be opaque or tinted with a material to block out the sun's harmful ultraviolet rays. Alternatively, the ear protector outer member 11 may be completely non transparent and colored with any desired or appropriate color. Such coloring, tinting or opaqueness is not a necessary element of the invention. However, the ability to ward off or block the sun's ultraviolet rays is an important characteristic of the invention. Regardless of the material from which the outer member 11 is made from, a UV blocking plastic film may be applied over the outer surface of member 11 to provide a blocking effect on the sun's rays.

A clip member 12 which is used to secure the outer member 11 to the hat itself is shown in FIG. 2 of the drawings. The cross-sectional shape of clip member 12 approximates that of the letter "J" having a substantially straight vertical portion 18, a substantially horizontal portion 19 and upwardly curved lower extending portion. It is desirable that clip member 12 have spring like characteristics. The horizontal portion 19 of clip member 12 is configured to fit over flange 17 of ear protector 11. The curved portion 21 of clip member 12 is configured to fit over the radiused bottom end of plastic portion 16 of ear protector 11. The vertical portion 18 of clip member 12, on its inside surface, may include a plurality of barb-like members 22 having a downwardly pointed edge so as to grab the inside of the headband in addition to relying upon the spring force of clip member 12 in order to secure the ear protector member 11 to the cap.

Figure 3:
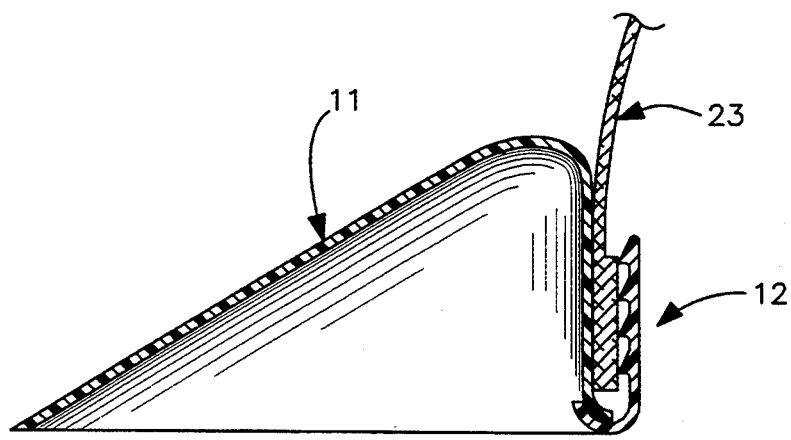
FIG. 3 is a cross-sectional view of the ear protector apparatus held in place to the headband of a cap by the clip member.

FIG. 3, in cross-section, shows the positioning of the inventive ear protector apparatus 10 to one side of the headband of a typical cap 23 to which the ear protective apparatus 10 is to be fitted. As previously explained, the actual position of the ear protector apparatus 10 is adjustably positioned along the headband of the cap 23 so as to fit the particular anatomy of the person wearing the hat. In this manner, the person wearing the hat 23 can position the ear protector apparatus 10 at a location precisely over his or her ears. FIG. 3 also shows the fitting of the outer ear protector member 11 secured by the spring clip 12 to the headband of cap 23. The grabbing effect of barb-like members 22 can also be seen in this view.

Figure 3A:
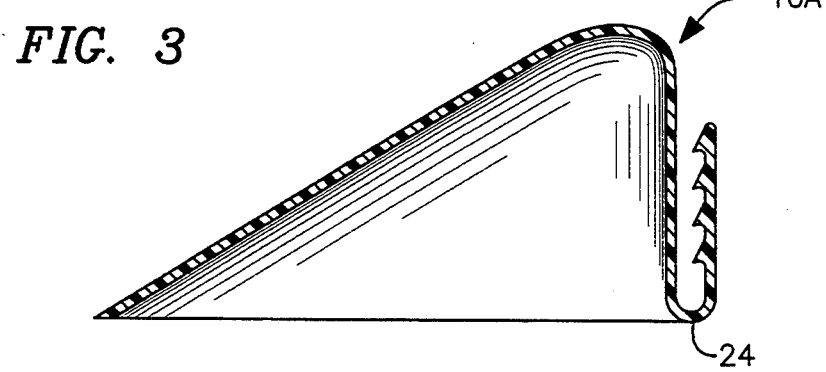
FIG. 3A is a one piece ear protector shown in cross section.

FIG. 3A shows in cross-section, the inventive ear protector apparatus 10A made in a single piece. That is, the ear protector member 11 is integrally or fixedly attached at its bottom 24 to clip member 12.

Figure 4:
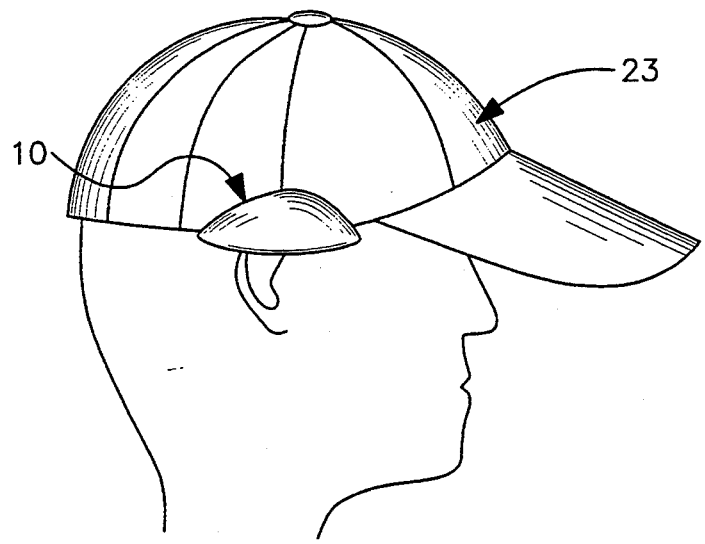
FIG. 4 is a side view of a typical cap having the ear protector of the present invention shown in place thereon.
Figure 5:
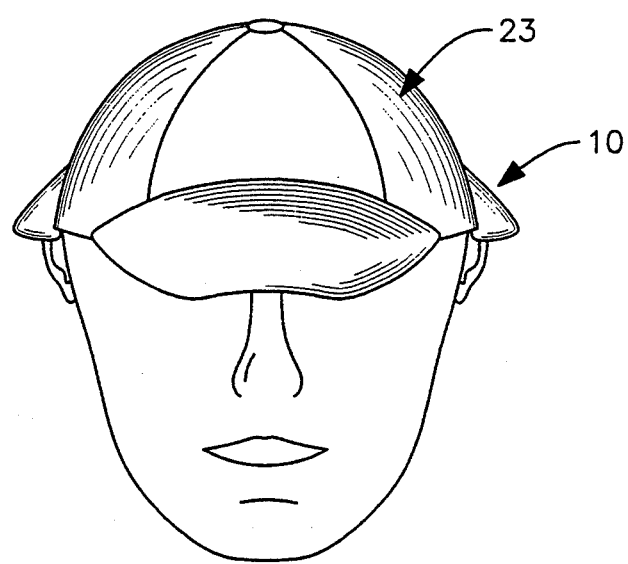
FIG. 5 is a front view of the cap of FIG. 4 showing the ear protectors in place as fitted to the head of a person and further illustrating the overhead protection afforded to a person's ears.

FIG. 4 shows a side profile view while FIG. 5 shows the front view of the cap 23 of FIG. 4 together with the ear protectors 10 fitted thereon as applied to a person's head. The unobstructive nature of the ear protectors 10 and the fit up of the same with reference to a person's ear can be seen in these figures.

Figure 6:
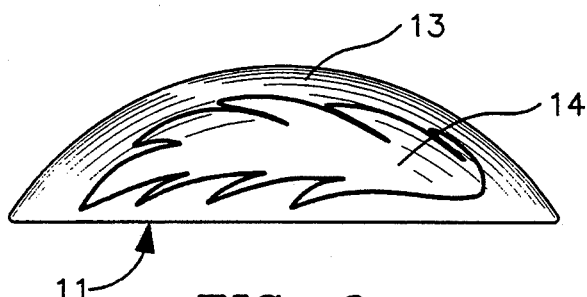
FIG. 6 is a side view of the ear protector showing an ornamental design thereof.

FIG. 6 shows a side profile of the outer surface 13 of the ear protector 10 along with a decorative logo 24 thereon. In the example shown, the decorative logo 24 comprises a wing which may for example be a logo of a sports organization. Alternatively, the logo 24 may comprise that of a business entity or even the name of a business entry. The ornamental decoration 24 may comprise a deal of a type which is well known and conveniently applied.

While this invention has been described, disclosed, illustrated and shown in certain terms or certain embodiments or modifications which it has assumed in practice, the scope of the invention is not intended to be limited nor should it be deemed to be limited thereby and such other modifications or embodiments as may be suggested by the teachings herein are particularly reserved especially as they fall within the breath and scope of the claims here appended.

I claim as my invention:

1. Ear protector apparatus adapted to be fitted to the headband of a hat and cover a person's ears from the sun's rays comprising:
   a convexly shaped ear protector member configured to cover the top portion of a person's ear,
   a plate member extending from a vertical edge of said ear protector member extending substantially vertically downward, and
   a clip member attached to a bottom of said plate member extending upward, said clip member being spring loaded relative to said plate member said clip member being movable away from and toward said plate member for creating an adjustable space therebetween for fitting therein a headband portion of a hat and whereby said ear protector apparatus is adjustable in position along the length of said headband.

2. The ear protector apparatus of claim 1 wherein said ear protector member, said plate member and said clip member comprise one integral piece.

3. The ear protector of claim 2 wherein said clip member includes one or more serrated edges along a planar surface thereof.

4. The ear protector apparatus of claim 1 wherein said ear protector member and said plate member comprise one integral piece and said clip member is a separately attachable member.

5. The ear protector apparatus of claim 4 wherein said clip member includes one or more serrated edges along a planner inside surface thereof.

6. The ear protector apparatus of claim 4 wherein said plate member includes a flange member extending outward from bottom of said plate member, said clip member includes upwardly curved portion configured to lockingly fit over said flange member.

7. The ear protector apparatus of claim 4 wherein said ear protector member is made from a material having a blocking effect on the sun's rays.

8. The ear protector apparatus of claim 4 including a film made from a material having a blocking effect on the sun'rays said film being fitted to a planar surface of said ear protector member.

9. The ear protector apparatus of claim 4 including a decorative design on a planar surface of said ear protector member.

* * * * *